United States Patent [19]

Kerwin

[11] Patent Number: 4,911,697
[45] Date of Patent: Mar. 27, 1990

[54] CHEST DRAINAGE UNIT HAVING INCREASED AIRFLOW CAPACITY WITH CAPABILITY TO DAMPON NOISE

[75] Inventor: Michael J. Kerwin, Ballwin, Mo.

[73] Assignee: Sherwood Medical Company, St. Louis, Mo.

[21] Appl. No.: 227,346

[22] Filed: Aug. 2, 1988

[51] Int. Cl.$^4$ ............................................. A61M 1/00
[52] U.S. Cl. .................................. 604/318; 604/319; 604/321; 137/205
[58] Field of Search ............... 137/205; 604/118, 119, 604/319-321, 318

[56] References Cited

U.S. PATENT DOCUMENTS 4,372,336  2/1983  Cornell ............................... 137/205
4,738,671  4/1988  Elliot ................................... 604/319

Primary Examiner—Jerome L. Kruter
Attorney, Agent, or Firm—Andrew J. Beck; Montgomery W. Smith; Richard D. Allison

[57] ABSTRACT

A chest drainage unit having a suction regulator in fluid communication with the suction control chamber for regulating the suction pressure applied to the pleural cavity of the patient wherein the suction regulator includes a valve device which provides a continuous amount of fluid communication between the atmosphere and the suction source in the normally closed position and being movable to an open position in response to the increased negative pressure to allow an increase in the amount of fluid communication between the atmosphere and the suction source.

7 Claims, 6 Drawing Sheets

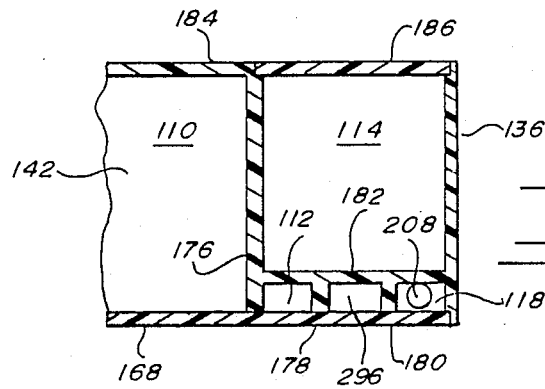
Fig. 4.
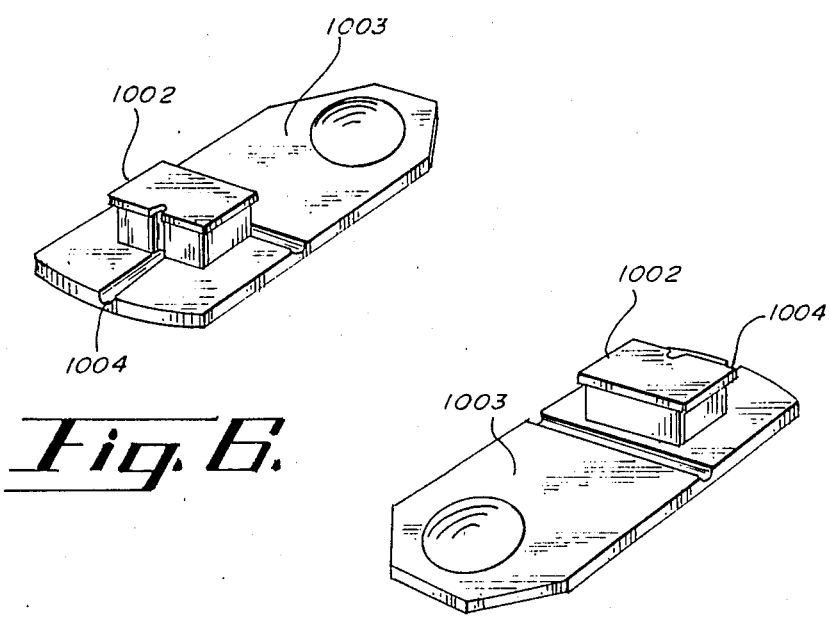
Fig. 6.
Fig. 7.

CHEST DRAINAGE UNIT HAVING INCREASED AIRFLOW CAPACITY WITH CAPABILITY TO DAMPON NOISE

BACKGROUND OF THE INVENTION

The present invention relates to an improved chest drainage unit, having an increased airflow capacity, which both operates noiselessly and maintains the patient vacuum at safe levels in the event of failure of the device that regulates the amount of suction applied throughout the unit during its normal course of operation.

A chest drainage unit is an apparatus for suctioning gases and liquids from the chest cavities, or pleural cavities of patients. The pleural or chest cavity lies within the rib cage above the diaphragm and is surrounded by a pleural membrane. The pleural cavity contains both lungs, which in their normal expanded state fill the pleural cavity. Several conditions and diseases such as emphysema and various infections can cause a build up of liquid and gases around the lungs in the intrapleural space. When this happens, it causes the lungs to collapse to a volume much less than that of the pleural cavity, severely impairing breathing functions. The lungs can be re-expanded to their normal state of filling the pleural cavity by draining the liquid and gases from the area outside the lungs using a chest drainage unit.

Chest drainage units are also used in the treatment of patients who have air leaks in their lungs, allowing gases to enter the intrapleural space. Gases can be evacuated by use of a chest drainage unit. In treating patients with air leaks, it is very important to maximize the flow of air through the chest drainage unit, especially in the case of patients with high volume air leaks. Patients with broncho-pleural fistulae may have very large air leaks, particularly if the disease is associated with adult respiratory distress syndrome. For these patients, rapid and complete removal of the intrapleural air is necessary to prevent formation of a pneumothorax and to keep the pleural surfaces in contact, so that adhesion formation and eventual healing of the broncho-pleural fistulae may be enhanced.

There has therefore been a great need for a chest drainage unit having an increased airflow capacity while maintaining the ability to operate noiselessly and without risk to the patient of exposure to excessive negative pressure, i.e., suction. The anxiety-provoking nature of noise in a hospital environment has been appreciated for some time (see, e.g., "The Perceptual World of the ICU," Gowan, March–April, 1979 issue of *Heart & Lung*, Vol. 8, No. 2, pp. 340–344). Also, it is well known that exposure of the patient's chest cavity to excessive negative pressure can cause the patient both severe discomfort and severe damage.

U.S. Pat. No. 4,372,336, issued to Cornell et al. and assigned to Sherwood Medical Industries, Inc., discloses and claims a chest drainage unit similar to that of the present invention but for the improvements disclosed and claimed herein. The specification of the '336 patent in columns 1 and 2 discloses the prior art which existed with respect to chest drainage units a the time the application for the '336 patent was filed. This disclosure is incorporated herein by reference.

The chest drainage unit of the '336 patent comprises a collection chamber for collecting blood and other liquids suctioned from the patient's pleural cavity, an underwater seal chamber having a liquid seal which acts as a one-way valve for passing gases from the patient's pleural cavity to the atmosphere, a manometer chamber which provides an accurate indicia of the level of suction being applied to the cavity to be drained, a suction control chamber for limiting the maximum suction applied to the patient's pleural cavity, and a combination vent valve-and-filter assembly which permits the venting of negative pressure in the collection chamber by simple push button step to admit filtered air to the collection chamber.

One of the advantages of the chest drainage unit of the '336 patent over the prior art at the time the application for that patent was filed was the employment of a suction control chamber which did not involve the bubbling of atmospheric air through a liquid, and thus avoided the noise caused by such bubbling. In the preferred embodiment of the apparatus of the '336 patent, the suction control chamber comprises a housing comprising upper and lower compartments separated in part by a diaphragm. The upper compartment is in fluid communication with both the source of suction and the underwater seal chamber, while the lower compartment is in fluid communication only with the atmosphere. A nozzle which extends into the upper compartment has disposed in it a reduced diameter orifice through which air and gases from the patient's chest cavity pass, and through which the collection and underwater seal chambers communicate with the suction source. The nozzle is vertically movable toward and away from the diaphragm in order to regulate the vacuum to which the patient's chest cavity is exposed.

When set at a pre-determined distance away from the diaphragm, corresponding to a pre-determined vacuum level, the negative pressure on the diaphragm from the suction source causes the diaphragm to bow up and eventually contact the orifice, shutting off the vacuum. Eventually the downward, i.e. positive pressure on the diaphragm caused by the accumulation of gases in the upper compartment causes the diaphragm to move away from the orifice again, re-establishing communication between the suction source and the underwater seal chamber. The constant movement of the diaphragm in response to the suction source, and the vibrations of the diaphragm in response to the forces treated by the flow of gases through the upper compartment, causes some noise, which is sufficiently dampened by an appropriately sized and configured outlet port in the lower compartment allowing for communication between such compartment and the atmosphere. The outlet port is large enough to allow the diaphragm to move freely and yet small enough to dampen the noise caused by the movement of the diaphragm.

Another advantage of the apparatus of the '336 patent over the prior art at the time the application for that patent was filed was its "fail safe" mode of operation which prevents the patient from being exposed to dangerous levels of suction in the event of failure of the suction regulator to operate correctly. In the unlikely event that the diaphragm of the suction regulator were to tear or break, the small outlet port in the lower compartment of the regulator chamber would allow enough atmospheric air into the upper chamber to communicate with the suction source and maintain the negative pressure on the patient's chest cavity at a safe level.

In working to further improve the unit disclosed in the '336 patent, it was determined that for a given negative pressure of source vacuum, the airflow capacity is limited by the reduced diameter of the orifice of the nozzle through which the suction source communicates with the underwater seal chamber. The only way to increase the airflow in that unit is to increase the diameter of the orifice in the nozzle. This change, however, if incorporated, could pose significant operational difficulties as well as danger to the patient, because neither the noise damping nor "fail safe" devices of the '336 apparatus would be fully effective in the presence of the substantially increased airflow caused by the increased orifice diameter. Increasing the diameter of the orifice in the nozzle could adversely affect the "fail-safe" function, in that if the diaphragm of the suction regulator should break or tear, the atmospheric port in the lower compartment of the suction regulator may be too small to allow enough air to communicate with the suction source to maintain the pressure in the patient's chest cavity at a safe, comfortable level. Furthermore, increasing the flow of air through the chest drainage unit of the '336 patent would increase the noise caused by the vibration of the diaphragm to an unacceptable level, which could not be effectively dampened by the mechanisms provided for therein. In such a case, the outlet port in the lower compartment of the housing of the suction regulator would be too large to dampen the increased amount of noise.

Before the chest drainage unit disclosed in the '336 patent, the goals of noiseless operation and a reliable fail safe mode were deemed incompatible in the prior art in the presence of a substantially increased air flow. Although the chest drainage unit disclosed in the '336 patent functions very well, the need still exists for a chest drainage unit having an increased air flow capacity for the rapid and complete removal of pleural air, which both operates noiselessly and maintains safe patient vacuum levels at all times, even if the suction regulator fails to function.

OBJECTS OF THE INVENTION

A object of the invention is to provide a chest drainage unit having an increased air flow capacity in comparison to prior art units, and which is noiseless in its operation despite its increased airflow capacity.

It is a further object of the present invention to provide a chest drainage unit which provides an adequate fail safe system so that there is no risk of discomfort to the patient in the event of failure of the device that regulates the amount of suction due to excessive patient vacuum levels.

SUMMARY OF THE INVENTION

The chest drainage unit of the present invention comprises casing having a collection chamber for receiving fluid to be drained from the chest cavity, means defining an inlet opening into the collection chamber for establishing fluid communication between the collection chamber and the patient's chest cavity, means defining an outlet adapted to be connected in fluid communication with the source of suction, means defining a liquid seal between the collection chamber an the outlet, and a suction regulator for limiting the amount of suction applied to the collection chamber through the outlet and liquid seal. The design of the suction regulator constitutes an improvement in the unit over the prior art in that it allows for an increased airflow between the collection chamber and the suction source while maintaining a predetermined patient vacuum. Despite the increased airflow through the unit, it operates noiselessly and provides an adequate fail safe system which prevents exposure of the patient's chest cavity to excessive uncomfortable vacuum levels in the event of failure of the suction regulator.

The increased airflow capacity of the present invention is achieved by increasing the diameter of the orifice in the nozzle which extends into the housing of the suction regulator and which is connected to the source of suction. The enlarged orifice produces higher levels of noise over a wider range of patient vacuum levels. In spite of this, noiseless operation of the unit is achieved by forcing the air under the vibrating diaphragm through a small outlet port defining a narrow passageway leading from the lower compartment of the housing of the suction regulator, which is not in communication with the source of suction, to the atmosphere. This passageway is large enough to allow the diaphragm to move freely in response to the pressure created by the source of suction, yet small enough to dampen the noise caused by the vibrations of the diaphragm. It is the only opening to the atmosphere from the regulator housing during the normal course of operation of the unit.

The larger orifice size poses a potential danger to the patient, especially when used in conjunction with a higher source vacuum, because upon failure of the diaphragm of the suction regulator, the patient's chest cavity will be exposed to the unregulated source vacuum, allowing a harmful build up of negative pressure in the chest cavity and a harmful amount of gases being removed. To compensate for this, the present invention employs a second larger outlet port or vent in the lower compartment of the regulator housing which communicates with the atmosphere, allowing more make-up air into the regulator housing in the event of failure of the diaphragm, and thus limits the vacuum to which the patient's chest cavity is exposed.

In order to ensure that the large atmospheric outlet port is only open in the fail safe mode, and thus does not interfere with the noise-damping function of the small outlet port during the normal course of operation of the unit, the invention includes means for selectively covering the large outlet port to prevent communication with the atmosphere during the normal course of operation of the unit, and opening such outlet port in response to negative pressure from the suction source in the event of a break or tear in the diaphragm, causing the failure of the diaphragm to effectively regulate the patient vacuum.

BRIEF DESCRIPTION OF THE DRAWINGS

FIG. 4 is a partial cross-sectional view taken along the plane 3—3 of FIG. 2 and looking in the direction of the arrows.

FIG. 6 is a perspective front view of the flapper valve employed in the preferred embodiment of the invention.

FIG. 7 is a perspective rear view of the flapper valve employed in the preferred embodiment of the invention.

DETAILED DESCRIPTION OF THE PREFERRED EMBODIMENT

Figure 1:
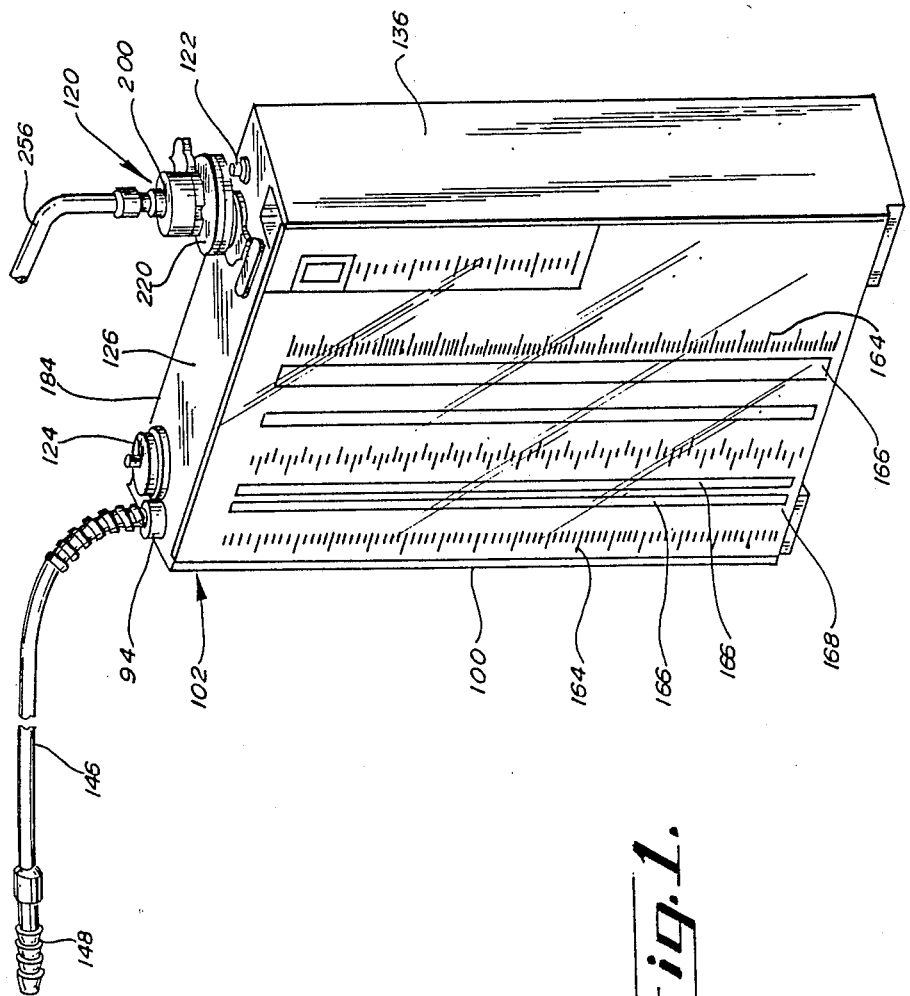
FIG. 1 is a perspective view of an improved chest drainage unit constructed in accordance with the teachings of the present invention.
Figure 2:
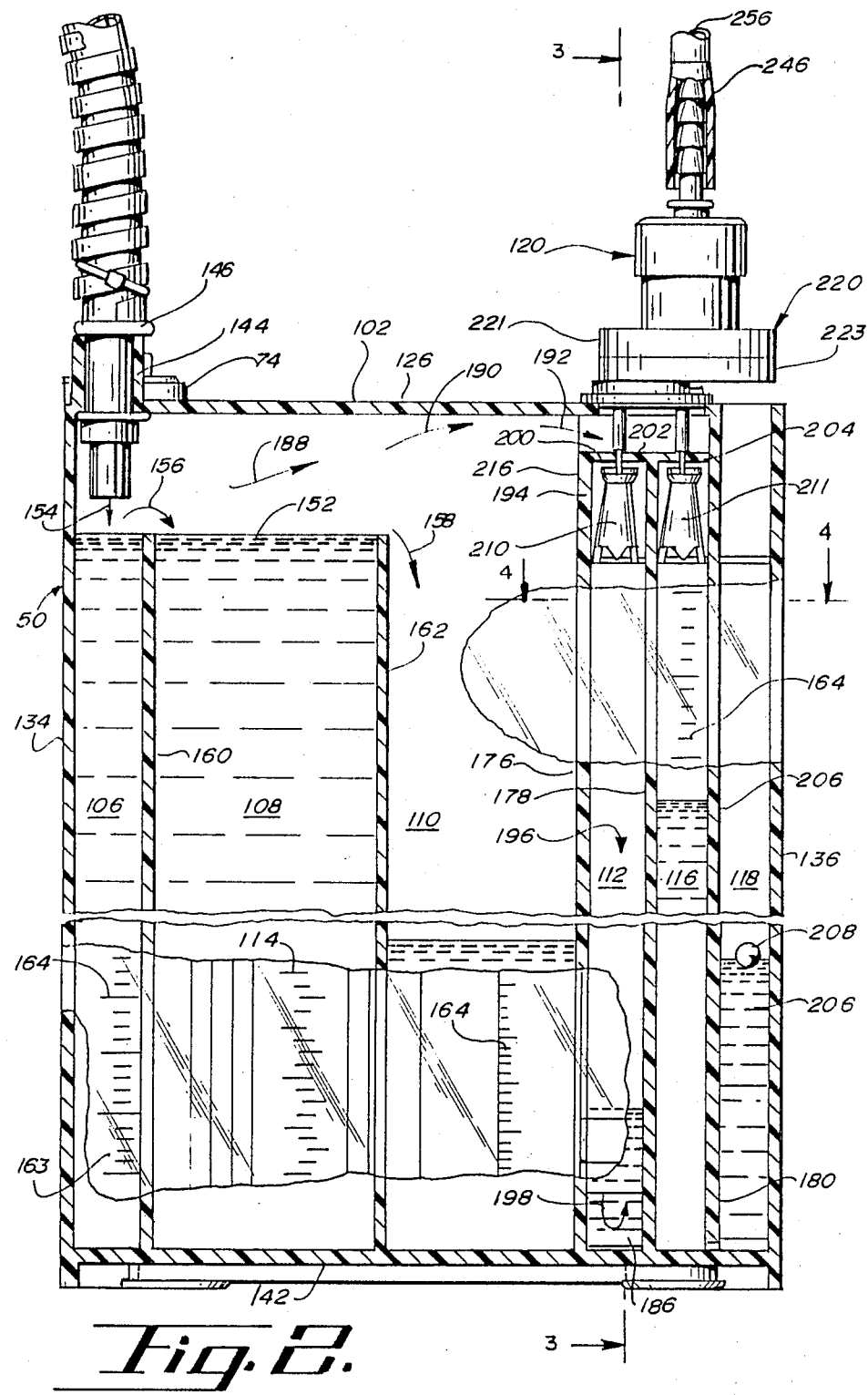
FIG. 2 is a front cross-sectional view of the unit shown in FIG. 1.

Referring to FIGS. 1 and 2, the improved chest drainage unit 100 constituting the preferred embodiment comprises a casing 102 having a top wall 126, a bottom wall 142, front and rear walls 168 and 184, respectively, and end walls 134 and 136. Interior partition 160, 162, 176, 178 and 180 (FIG. 2), all parallel to end walls 134 and 336, and a partition 182 (FIG. 3), which is parallel to front and rear walls 168, 184, divide the interior of casing 102 into a plurality of compartments, 106, 108, 110, 112, 114, 116 and 118.

Compartments 106, 108 and 110 constitute the collection chamber of the system; compartments 112 and 114 (best shown in FIGS. 2 and 3) constitute the underwater seal chamber; and compartments 116 and 118 comprise the manometer chamber of the system.

The system further comprises a suction regulator 120, a pop-off type safety valve 122 and a combination vent valve and filter unit 124, all mounted in the top wall 126 of the casing 102.

As best shown i FIG. 1, gradations 164 and writing surface material 166 are provided on the front wall 168 of the casing 102. The gradations indicate of the levels of liquid in the various compartments; and the writing surface material facilitates the marking of the level of liquid (e.g., blood, etc.) collected in the compartments 106, 108 and 110 of the collection chamber, at selected time intervals.

As best shown in FIGS. 1 and 2, the top wall 126 of the casing 102 is provided with a fitting 144 for receiving the outer end of a latex tube 146. The other end of the latex tube 146 is provided with an adapter 148 designed for connection to a thoracic catheter (not shown) leading to the patient's chest cavity to be drained.

With reference to the collection chamber 106, 108 and 110 (best shown in FIG. 2), the partitions 160, 162 divide the chamber into compartments 106, 108 and 110, to facilitate periodic monitoring of the level of liquid collected from the patient's cavity. As shown by arrows 154, 156 and 158 in FIG. 2, blood and other liquid 152 from the patient's chest cavity, via latex tube 146, drop into the compartment 106. When the compartment 106 is filled, the liquid will overflow into compartment 108 until that compartment is filled, whereupon additional liquid will overflow partition 162 and drop into compartment 110.

Figure 3:
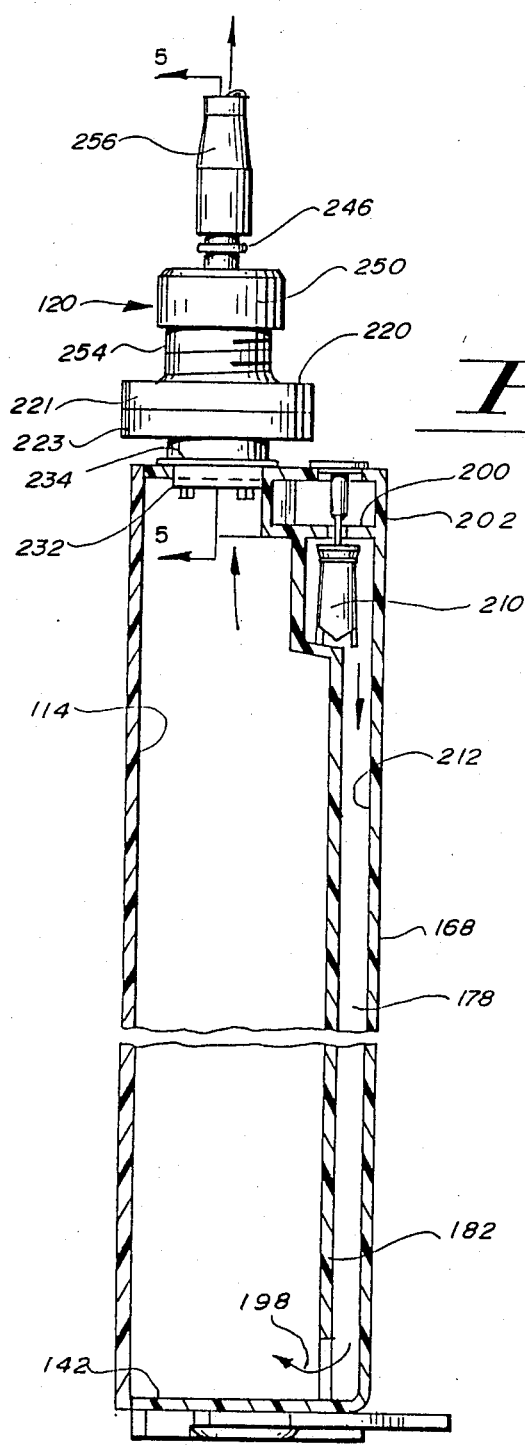
FIG. 3 is a side cross-sectional view taken along the plane 2—2 of FIG. 2.

The underwater seal chamber, comprising compartments 112 and 114, is best shown in FIGS. 2, 3 and 4. The compartments 112 and 114 communicate with one another by virtue of the fact that the partition 182 terminates above the bottom wall 142 (FIG. 3). Liquid (e.g., water 186; FIG. 2) is disposed in the bottom of the chamber and functions as a liquid seal permitting the flow of gases from the patient's chest cavity to atmosphere, but preventing reverse flow of gas. The flow path of gases suctioned from the patient's pleural cavity via latex tube 146 is shown by arrows 188, 190, 192, 194, 196 and 198 in FIGS. 2 and 3.

As best shown in FIG. 2, the upper end of the compartment 112 communicates with the collection chamber 106, 108, 110 through an opening 200 in a horizontal wall 202 which covers the upper ends of compartment 112 of the underwater seal chamber and compartment 116 of the manometer chamber.

With reference to FIG. 3, the upper end of the other, larger compartment 114 of the underwater seal chamber 112, 114 communicates with the suction regulator 120.

The two compartments 116, 118 of the manometer chamber also communicate with one another at their bottoms since the partition 180 separating the compartments 116 and 118 terminates above the bottom wall 142, as best shown in FIG. 2. The upper end of compartment 118 communicates with the atmosphere (see FIGS. 1 and 2) and the upper end of the compartment 11 communicates with the collection chamber 106, 108, 110 through an opening 204 in the horizontal wall 202.

A quantity of liquid 206 is disposed in the bottom of the manometer chamber 116, 118 to indicate the negative pressure being applied to the patient's chest cavity; and a dye ball 208 is provided in the compartment 118 to color the liquid (e.g., water) disposed in chamber 116, 118 to facilitate reading of the pressure level via graduations 164 on the portion of the front wall 168 which overlies the compartment 116.

As illustrated in FIGS. 2 and 3, a float valve 210 is provided at the upper end of compartment 112 of the underwater seal chamber 112, 114; and an identical float valve 211 is provided at the upper end of compartment 116 of the manometer chamber 116, 118. These float valves 210 and 211 prevent the expulsion of the liquid 186 and 206, respectively, from their respective compartments 112 and 116. The structure and function of the float valves are described in detail in the specification of the '336 patent at columns 5-6, and in the drawings referred to therein. These descriptions are incorporated herein by reference.

Suction is applied to the patient's pleural cavity, via the underwater seal chamber 112, 114, the collection chamber 106, 108; 110 and the latex tube 146, by means of a suitable suction source (not shown); nd the suction regulator 120 provides for convenient and accurate regulation of the level of suction applied to the patient.

Figure 5:
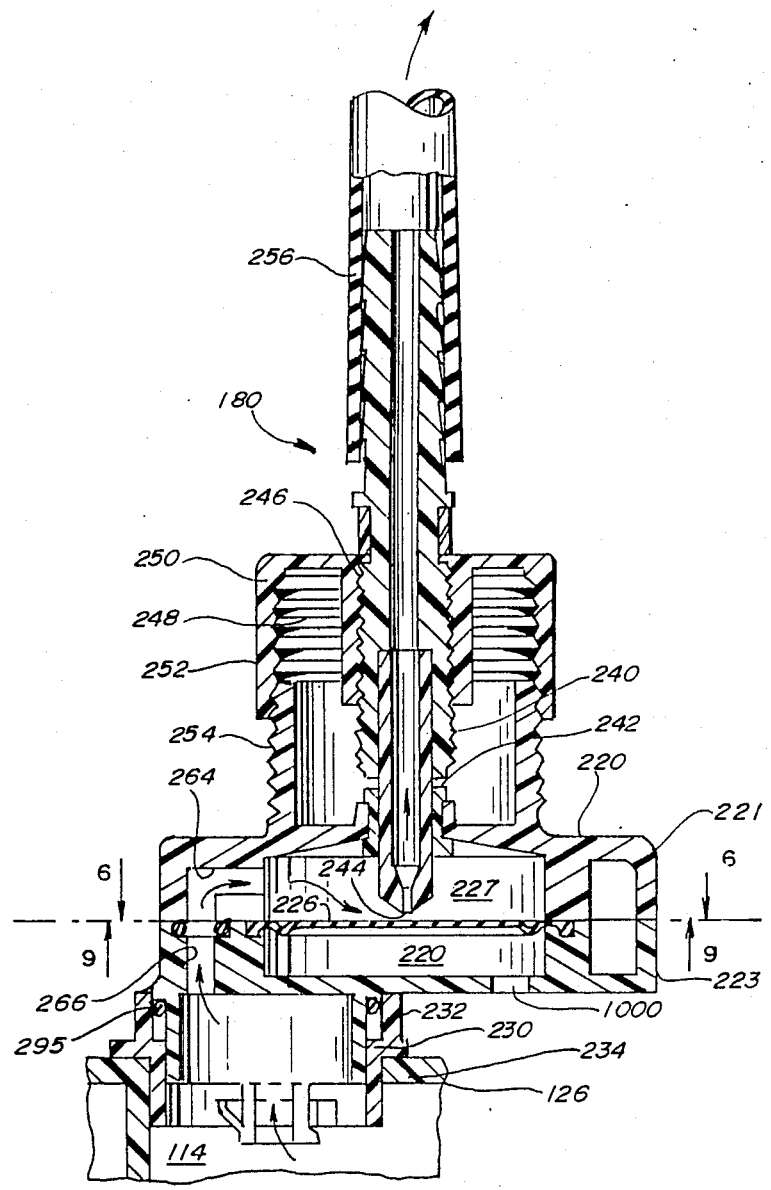
FIG. 5 is a cross-sectional view of the suction regulator taken along the plane 4—4 of FIG. 3 and looking in the direction of the arrows.

The suction regulator 120, best illustrated in FIG. 5 includes a housing 220 which encloses a suction regulating chamber comprising an upper compartment 222 and a lower compartment 224, separated by a flexible diaphragm 226. The upper compartment 222 of regulator chamber 222, 224 is in fluid communication with the compartment 114 of the underwater seal chamber 112, 114 by means of passages 264, 266 which extend through the regulator housing 220, as shown in FIG. 5. When the chest drainage unit 100 is operating, suction from a suitable source will be applied, via tube 256, tubular stem 240, upper compartment 222, and passages 264 and 266, to the compartment 114 of the underwater seal chamber 112, 114, as illustrated by the flow arrows in FIG. 5.

The lower compartment 224 is in fluid communication with the atmosphere through an L-shaped passageway 1004 in a valve 1003 which fills an outlet port in the bottom of the regulator housing (FIGS. 6, 7, 8(a) and 8(b)), and is separated from communication with the suction source by the flexible diaphragm 226.

A downwardly projecting boss 230 on the bottom of the regulator housing 220 (FIG. 5) extends through a fitting 23 which, in turn, extends through an opening 234 in the top wall 126 of the casing 102 above the compartment 114 of the underwater seal chamber 112, 114. A sealing rig 295 is disposed between the boss 230 and the fitting 232 to provide a fluid tight connection therebetween.

A vertically movable nozzle member 240 is slidably disposed in a bushing 242 in the upper end of housing 220 and extends into the upper compartment 222 of the regulator chamber 222, 224. An enlarged orifice 244 (as compared with the reduced diameter orifice 194 defined in U.S. Pat. No. 4,372,336), having a diameter of approximately 0.055 in., is provided in the forward end (or lower end, as viewed in FIG. 5) of the tube 240 in relatively close proximity to the diaphragm 226. The enlarged orifice size allows for an increased minimum airflow of 10 Lpm while maintaining a patient vacuum of 20 cm water when the suction source is set at 300 mm Hg.

The rear or upper end of the tube 240 is retained in a tubular adapter 246 which is externally threaded and received in an internally-threaded boss 248 of a regulator control knob 250.

The regulator control knob 250 has an outer peripheral wall 252 which is internally threaded and fits over an upwardly extending, externally threaded boss 254 on the upper end of regulator housing 220. This double-threaded arrangement (i.e., with mating threads on the fitting 246 and the interior boss 248 of knob 250, and the mating threads of peripheral wall 252 of knob 250 and the boss 254) permits vertical movement of the regulator tube 240 toward and away from diaphragm 226 by rotating the regulator control knob 250.

The upper end of fitting 246 is adapted to be received in the outer end of a tube 256 which is connected to a source of suction such as a hospital suction supply.

The degree of suction may be regulate by moving the enlarged diameter orifice 244 on the forward end of tubular stem 240 closer to or further from the diaphragm 226 by rotating the regulator adjustment knob 250 in a clockwise or counterclockwise direction.

When the suction (or negative pressure) being applied reaches a predetermined level, determined by the distance between orifice 244 and diaphragm 226, the central portion of the diaphragm will be sucked against orifice 244 to block off further suction. The central portion of the diaphragm 226 will remain in blocking engagement with the orifice 244 until the negativity in the collection chamber 106, 108, 110 and the patient's cavity being drained drops below the predetermined level (which will occur relatively quickly if air is leaking into the cavity).

When the degree of suction or negativity drops below the predetermined level, the elasticity of the diaphragm 226 will return the central portion of the diaphragm to its at-rest position, away from the orifice 244, to gain establish communication between the suction source and the compartment 114 of the underwater seal chamber 112, 114.

Figure 8A:
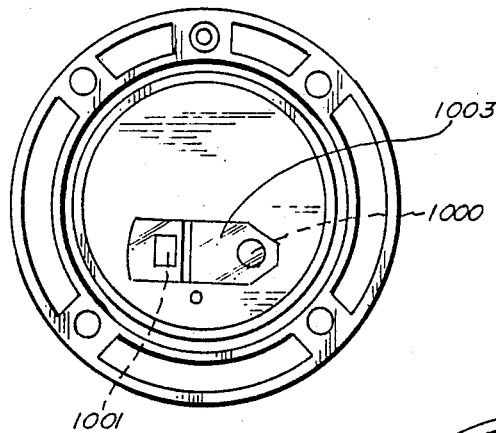
FIG. 8(a) is a top view of the inside of the lower compartment of the suction regulator, employed in the preferred embodiment of this invention, taken along the plane 6—6 of FIG. 5 (Diaphragm is not shown).
Figure 8B:
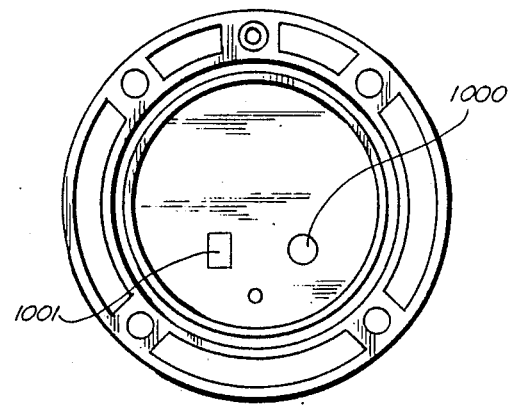
FIG. 8(b) is the same as FIG. 8(a), except that the lower compartment of the suction regulator is depicted without the flapper valve, in order to show the surface over which such valve is placed.
Figure 9:
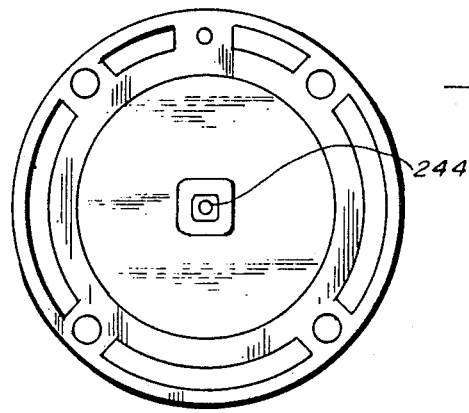
FIG. 9 is a bottom view of the upper compartment of the suction regulator employed in the preferred embodiment of the invention, taken along plane 9—9 of FIG. 5.

As shown in FIG. 8(b), the lower compartment 224 of the suction regulator chamber 222, 224 has two outlet ports 1000 and 1001 in the lower wall of the regulator housing 220 which, when unfilled or uncovered, leave the lower compartment open to the atmosphere. A plastic flapper valve 1003 (FIGS. 6, 7 and 8(a)) is positioned on the inside of the lower compartment of the suction regulator flat against and covering port 1000 and preventing communication through that port between the atmosphere and such compartment. A protruding member 1002 of the valve extends from a portion of the flat valve surface adjacent to port 1000, and protrudes through port 1001 to the atmospheric side of such port. Such protruding member completely occupies the volume of the port 1001 except for the volume defined by a narrow L-shaped passageway 1004, which has a rectangular cross-section approximately 0.010 inches 0.025 inches, which extends down one side of the protruding member from the atmospheric side of the port to the interior of the lower compartment of the regulator housing, and then continues in a perpendicular direction along the surface of the flapper valve which lies flat against the interior surface of the housing. The protruding member 1002 anchors the flapper valve 1003 to the interior of the housing. Because the narrow L-shaped passageway is open to the atmosphere at all times during the course of operation of the chest drainage unit, it allows the diaphragm 226 to move freely and dampens the noise caused by its vibrations.

Outlet port 1000 is covered by the flapper valve 1003 during the normal course of operation of the unit. However, in the event of a break or tear in the diaphragm 226, the flapper valve 1003 will bend away from such port in response to the suction source, allowing enough atmospheric air to pass through the regulator to the suction source to maintain the patient vacuum at a safe level.

The means by which the suction regulator 120 is attached to and retained in the to wall 126 of the casing 102 of the chest drainage unit is described in detail in the specification of the '336 patent in columns 7 and 8. This description is incorporated herein by reference.

The chest drainage system of the present invention also incorporates a vent valve-and-filter assembly 124 (FIG. 1), which permits ready and convenient venting of the collection chamber 106, 108, 110 to filtered, atmospheric air. The structure and function of the vent valve-and-filter assembly is described in detail in the specification of the '336 patent in columns 8 and 9, and the drawings referred to therein. This description is incorporated herein by reference.

A pop-off valve assembly 122 (FIG. prevents the positive pressure inside the compartment 114 of the underwater seal chamber 112 and 114 from exceeding a predetermined safe level. The structure and function of this assembly is described in detail in the specification of the '336 patent in column 9, and the figures referred to therein. This description is incorporated herein by reference.

OPERATION

The operation of the chest drainage unit described above according to the invention is illustrated hereafter with respect to a preferred embodiment having an orifice 244 of approximately 0.055 inches diameter. The invention is not limited to the flow rates and vacuum levels described for illustrative purposes only.

In use, the outer end of the latex tube 146 is attached to a thoracic catheter (not shown) which, in turn, is inserted in the patient's chest cavity (e.g., pleural cavity) to be drained; and the other end of the tube 146 is attached to the casing 102 via the fitting 144. The tube 26 leading from the regulator 120 is connected to a suitable source of suction such as a hospital suction source.

When the suction source is set at 300 mm Hg, the chest drainage system will have an airflow capacity of a minimum of 10 Lpm while maintaining a patient vacuum of 20 cm water negativity.

Water (or other liquid) 186 and 206 will previously have been poured into the bottom of the underwater seal chamber 112, 114 and the bottom of the safety seal/manometer chamber 116, 118. The water may be colored if desired to facilitate monitoring of the drainage process.

The desired level of suction of negative pressure is set by rotating the control knob 250 of the suction regulator 120 to move the enlarged orifice 244 of the regulator nozzle 240 to a predetermined distance from the diaphragm 226 (FIG. 5).

The increased airflow capacity will cause increased vibrations of the diaphragm of the suction regulator. In the preferred embodiment of the present invention, the noise which would otherwise result from such vibrations will be dampened by forcing the air under the diaphragm in the lower compartment of the suction regulator through a narrow L-shaped passageway defined by a groove which extends along a portion of the plastic flapper valve which lies flat against the inside surface of the compartment and extends in a perpendicular direction along the part of the valve which protrudes through outlet port 1001 to the atmospheric side of the housing. This L-shaped passageway will not only force the air to pass through a narrow passageway, but also to change directions, thus damping the noise which would otherwise be produced by the vibrating diaphragm.

Suction applied through the regulator 120 will be reflected through compartment 114 (FIG. 3), the liquid seal 186, compartment 112, collection chamber 106, 108, 110, thoracotomy tube 146 and the patient's cavity to be drained.

Liquid and gases sucked from the cavity will enter the casing 102 through the thoracotomy tube 146. The liquid (e.g. blood) will drop into chamber 106, and will overflow into compartments 108 and 110, as illustrated by arrows 156 and 158 (FIG. 2).

Gases suctioned from the cavity will travel across the upper portion of the collection chamber 106, 108, 110, as illustrated by arrows 188, 190 and 192 in FIG. 2, and will travel through the opening 200 in horizontal wall 202, down through the compartment 112, as illustrated by arrows 196 and 198 in FIG. 2, will bubble through the liquid seal 186, and pass up through the compartment 14, as shown in FIG. 3, and out through the suction regulator 120.

The liquid 206 in the safety seal manometer chamber 116, 118 will rise in the compartment 116 and fall in the compartment 118 when suction is applied, since the compartment 116 is in fluid communication with the underwater seal chamber 112, 114 and the suction regulator 120, via the openings 204 and 200 in the horizontal wall 202 (FIG. 2), to indicate the level of suction in the system.

In the event the negativity in the collection chamber 106, 108, 110 rises to such a level that it would otherwise suck the liquid 186 and 206 from compartment 112 and 116, the liquid will raise the float valves 210 and 211 to close off the openings 200 and 204 and prevent expulsion of the water therefrom.

In the event that the diaphragm should tear or break, thus failing to respond to the negative pressure of the suction source by contacting the nozzle orifice at a pre-determined level of suction to shut off the vacuum, the lower compartment of the regulator housing will be in communication with the suction source, and the flapper valve will respond by lifting up and opening outlet port 1000 to allow a flow of atmospheric air to communicate with the suction source, thus maintaining the vacuum to which the patient's chest cavity is exposed to a safe maximum of 20 cm water negativity.

It is contemplated, of course, that various modifications may be made to the particular embodiment illustrated in the drawings and described above without departing from the spirit and cope of the invention. Accordingly, it is intended that the scope of this patent be limited only by the scope of the claims.

EXAMPLE I

Five prototype regulators were manufactured and then bench tested on June 13, 1985. The wall source vacuum was set at a static 300 mm Hg by connecting the chest drainage unit to the house vacuum system through an Ohio Suction Regulator Model #306-1008-880 before flow test. The Ohio suction regulator is commonly used in hospitals. The static airflow rates were measured using Gilmont #3 and #4 flow meters (0–12 Lpm and 0–33 Lpm airflow rates, respectively). The regulators achieved 10.9 Lpm average airflow at 225 mm Hg source vacuum (because the Ohio Suction Regulator was unable to maintain the static 300 mm Hg setting at 10.9 Lpm airflow). Additionally, with the maximum source vacuum applied to the regulator through the Ohio Suction Regulator (225 mm Hg), the patient vacuum level in the failsafe mode averaged 19 cm water negativity under the condition of a no-patient air leak.

What is claimed is:

1. In a chest drainage apparatus having a collection chamber therein for receiving fluid to be drained from a chest cavity, and a suction regulator for limiting the amount of suction applied to said collection chamber, said suction regulator comprising a pressure responsive diaphragm responsive to suction above a pre-determined level in said collection chamber to prevent suction above said pre-determined level being applied to said collection chamber until the suction in said collection chamber drops to about said pre-determined level, and a nozzle including an outlet opening exposed adjacent one surface of said flexible diaphragm, whereby suction above said pre-determined level at said one surface of said diaphargm in the vicinity of said nozzle with move a portion of said diaphragm against said nozzle outlet, and a means for manually moving said nozzle toward and away from said flexible diaphragm so as to vary said pre-determined level of suction at which said diaphragm in the vicinity of said nozzle will move against said nozzle outlet;

the improvement comprising:
means defining a small outlet opening from said regulator which is in fluid communication with the atmosphere, and which is small enough to effectively dampen the noise created by the vibrations of said diaphragm;
means defining a large outlet opening from said regulator which allows for fluid communication bewteen said regulator and the atmosphere, and which is sufficiently large so that in the event of failure of said diaphragm to regulate the amount of suction applied to said patient's chest cavity, the flow of atmospheric air therethrough to enter said regulator will relieve the negative pressure on said patient's chest cavity and maintain it at a safe level; and a means for selectively covering said large outlet opening wherein said means includes a body portion having a passageway therein wherein said passageway provides a small amount of continuous fluid communication between the atmosphere and said suction source and wherein said body portion is normally disposed to substantially restrict fluid communication through said large outlet opening and being movable to a non-restricting position in the event of failure of said diaphragm.

2. The apparatus of claim 1, wherein the diameter of said nozzle outlet is about 0.05 inches.

3. The apparatus of claim 1, wherein said large outlet from said regulator housing has a diameter greater than 0.125 inches.

4. The apparatus of claim 1, wherein said nozzle outlet has a diameter sufficiently large to provide a minimum airflow capacity of 10 liters per minute (Lpm) between said collection chamber and said source of suction, while maintaining a patient vacuum of about 20 cm water negativity.

5. The apparatus of claim 1, wherein said small outlet from said regulator housing has a cross-sectional area less than about 0.0002 square inches.

6. The apparatus of claim 1, wherein the means for selectively covering is a valve made of a flexible material comprising:

a body portion which lies against said large outlet opening on the inner surface of said regulator housing during the normal course of operation of said chest drainage unit, and which responds to the negative pressure exerted by said suction source in the event of failure of said diaphragm by bending away from said large outlet opening and establishing fluid communication through said large outlet opening between the atmosphere and said suction source; and a protruding member which extends from a portion of the body portion of said valve adjacent said large outlet opening.

7. The apparatus of claim 6 wherein said passageway on said body portion is an L-shaped passageway, which extends along a portion of the body portion of said valve and perpendicularly down along the side of said protruding member, establishing fluid communication between the atmosphere and said regulator housing.

* * * * *